United States Patent [19]

Ballintyn et al.

[11] 4,351,069
[45] Sep. 28, 1982

[54] PROSTHETIC DEVICES HAVING SINTERED THERMOPLASTIC COATINGS WITH A POROSITY GRADIENT

[75] Inventors: Nicolaas J. Ballintyn, Somerville; Michael J. Michno, Jr., Bridgewater, both of N.J.

[73] Assignee: Union Carbide Corporation, Danbury, Conn.

[21] Appl. No.: 103,399

[22] Filed: Dec. 13, 1979

Related U.S. Application Data

[63] Continuation-in-part of Ser. No. 53,192, Jun. 29, 1979, abandoned.

[51] Int. Cl.³ .................. A61F 1/24; A61F 5/04; A61B 17/18; A61C 13/20
[52] U.S. Cl. .................................... 3/1.912; 3/1.9; 3/1.91; 128/92 B; 128/92 BC; 128/92 C; 433/173; 433/176; 433/201; 156/77; 264/25; 264/327
[58] Field of Search .................. 3/1.9–1.913, 3/1; 128/92 C, 92 CA, 92 B, 92 BA, 92 BB, 92 BC; 433/173–176, 201

[56] References Cited

U.S. PATENT DOCUMENTS 3,855,638 12/1974 Pilliar ................................ 3/1
3,986,212 10/1976 Sauer .............................. 3/1.91
4,164,794 8/1979 Spector et al. ................ 3/1.912

FOREIGN PATENT DOCUMENTS 2306552 8/1974 Fed. Rep. of Germany ........ 3/1.91

OTHER PUBLICATIONS

Williams et al., Implants in Surgery, W. B. Saunders Co., Ltd., pp. 89–93, published Jul. 3, 1973.
Sauer et al., "The Role of Porous Polymeric Materials in Prosthesis Attachment", presented at the Clemson University Fifth Annual Biomaterials Symposium, Apr. 14–18, 1973.
Spector, M. et al., "Bone Growth into Porous High-Density Polyethylene", J. Biomed. Materials Res. Symposium, No. 7, pp. 595–603, 1976.

Primary Examiner—Ronald L. Frinks
Attorney, Agent, or Firm—Donald M. Papuga

[57] ABSTRACT

Coated Prosthetic devices useful in the medical and dental fields, such as dental implants, intramedullary nails, and total hip prostheses, are provided having a porosity or density gradient in the sintered plastic coating. The higher porosity is at the outer surface which facilitates bone ingrowth while the lesser porosity which has a higher density and a more continuous plastic layer is on the inner surface and thus provides better adhesion to the load bearing component.

20 Claims, 2 Drawing Figures

PROSTHETIC DEVICES HAVING SINTERED THERMOPLASTIC COATINGS WITH A POROSITY GRADIENT

This application is a continuation-in-part of Ser. No. 053,192 filed June 29, 1979, now abandoned.

This invention relates in general to improved prosthetic devices. In one aspect, this invention relates to prosthetic devices which have sintered, thermoplastic coatings. In a further aspect, this invention relates to improved prosthetic devices wherein there is a porosity or density gradient in the sintered thermoplastic coating. The invention is also directed to a process for preparing the sintered coatings.

Prior to the present invention various methods have been disclosed in the literature for the attachment of prosthetic devices to the musculoskeletal system. These methods can be categorized as involving: (1) impaction; (2) nails and screws; (3) cement; and (4) porous surface materials. The use of porous surface implants for fixation has been recognized as potentially providing significant advantages, however, this technique has not been generally accepted by the surgical community because of problems of early fixation and long term stability associated with such devices.

Various devices known to date include those described in U.S. Pat. No. 3,986,212 which issued Oct. 19, 1976 to B. W. Sauer describing composite prosthetic devices containing a porous polymeric coating for bone fixation by tissue ingrowth. The porous polymeric materials which are indicated to be useful are these having a specified density and interconnected pores of a specific average pore diameter. Among the polymeric materials disclosed are high density polyethylene and polypropylene or mixtures thereof having certain critical parameters. It is also indicated that the coatings can be mechanically interlocked or chemically bonded to the device.

U.S. Pat. No. 3,971,134 which issued July 27, 1976 to J. C. Bokros relates to a dental prosthesis for permanent or prolonged implantation in a jawbone of a living body. The implant can be coated with such materials as vinyl polymers e.g., acrylic polymers, polyethylene and carbon fiber filled Teflon.

J. Galante, et al, in J. Bone and Joint Surgery, 53A, No. 1,101 (1971) describes sintered fiber metal composites as a basis for attachment of implants to bone and U.S. Pat. No. 3,808,606 which issued on May 7, 1974 to Raymond G. Tronzo describes stainless steel and cobalt-chromium-molybdenum alloy prostheses possessing porous surfaces for fixation by tissue ingrowth.

Also, of general interest are U.S. Pat. Nos. 3,992,725 "Implantable Material and Appliances and Method of Stabilizing Body Implants", which issued on Nov. 23, 1976 to C. A. Homsy, U.S. Pat. No. 3,909,852 "Implantable Substitute Structure for at Least Part of the Middle Ear Bony Chain" which issued Oct. 7, 1975 to C. A. Homsy, and U.S. Pat. No. 3,971,670 "Implantable Structure and Method of Making Same" which issued July 27, 1976 to C. A. Homsy.

In addition to patents, various articles have appeared in the literature relating to bone ingrowth into porous materials. Typical articles include, among others, S. F. Hulbert, "Attachment of Prostheses to the Musculoskeletal System by Tissue Ingrowth and Mechanical Interlocking", J. Biomed. Mater. Res. Symposium, 4, 1 (1973); M. Spector, et al, "Bone Growth into Porous High-Density Polyethylene", J. Biomed. Mater. Res. Symposium, 7, 595 (1976); C. A. Homsy "Implant Stabilization-Chemical and Biomedical Considerations", Orthopedic Clinics of North America, 4, No. 2,295 (1973) and J. N. Kent, et al, "Proplast in Dental Facial Reconstruction", Oral Surgery, Oral Medicine, Oral Pathology 39, No. 3, 347 (1975).

However, the porous materials disclosed in the literature as being useful for prosthetic devices provide inappropriate biomechanical environments leading to either of two undesirable situations. First, low modulus-high creep porous coatings such as porous Teflon/graphite composites, exhibit metastable fibrous tissue in the pores after extended periods. This tissue is not suited to support load bearing joint prostheses. The fibrous tissue is a metastable precursor to bone and under normal physiological conditions (including physiological loading conditions) would remodel to bone. The high loads transmitted through low modulus materials and the excess creep result in fibrous tissue which fails to remodel to bone. Other low modulus-high creep materials employed for prosthetic devices include polyethylene and polypropylene.

Secondly, high modulus materials such as ceramics ($16 \times 10^6$ psi) and metals like titanium ($17 \times 10^6$ psi) and cobalt-chromium-molybdenum alloy ($34 \times 10^6$ psi), do not spread sufficient load to the ingrown or surrounding bone to prevent resorption. In porous metal and ceramic coated femoral and humeral stems, load is concentrated at the apex of these prosthetic components causing stress concentrations in the surrounding bone and subsequent resorption. In addition, the bone spicules in the pores of these porous ceramic and metallic implants do not experience loads, thereby resorbing. The loss of bone from the pores in areas of porous implants which experience no load has been demonstrated histologically. This type of bone loss leads to a decrease in composite strength (e.g. interfacial shear strength) and a subsequent decrease in "in use" performance in these high modulus porous materials.

The above-cited patents and literature describe the use of porous coatings on prostheses and describe acceptable pore size range requirements. However, it has been found that metals, ceramics and polymers such as the vinyl polymers, polyethylene, polypropylene, carbon filled Teflon and others disclosed as being useful for coating prosthetic devices do not establish the proper biomechanical environment to achieve appropriate early fixation, long-term stability and strength at the bone-prosthesis interface. Previously described polymeric materials can also lack the toughness, creep resistance, tensile and impact strength and steam sterilizability to be acceptable as the polymer of choice for coating prosthetic devices. Even select high density polyethylene and polypropylene porous compositions, stated to possess the right amount of flexibility and strength have not met with general acceptance.

More recently, prosthetic devices have been devised which have a coating of porous bioengineering thermoplastic materials, such as a polysulfone, and which after implantation achieve a long-term bone fixation by ingrowth of tissue and subsequent remodeling to bone. Such devices are described in U.S. Pat. No. 4,164,794 by Mr. Spector et al. and entitled "Prosthetic Devices Having Coatings of Selected Porous Bioengineering Thermoplastics". It is indicated therein that the coating can be applied either by a sintering technique or by a foam process to provide certain physical properties in the coating which optimize tissue ingrowth, remodeling to bone and long-term bone fixations.

It has now been found that improved results are obtained in prosthetic devices having a sintered coating of a bioengineering thermoplastic material, when a porosity gradient exists across the coating thickness. A higher porosity at the outer side facilitates bone ingrowth while a lesser porosity on the inner side provides better adhesion to the load bearing component with greater stiffness and strength.

Accordingly, one or more of the following objects can be achieved by the practice of this invention. It is an object of the invention to provide prosthetic devices comprised of an inner load bearing functional component and an outer sintered coating of selected bioengineering thermoplastics, having a porosity gradient over at least a portion thereof. Another object of this invention is to provide coated prosthetic devices which after implantation achieve a long-term bone fixation by ingrowth of tissue into and through a select porous bioengineering thermoplastic coating with subsequent remodelling to bone. A further object is to provide a prosthetic device having a coating of a specified porosity and porosity gradient which provides the optimum substrate for tissue ingrowth. Another object is to provide prosthetic devices wherein the coating exhibits sufficient tensile and impact strength during and after bone formation to accommodate applied loads during insertion and after surgery. Another object of this invention is to provide porous bioengineering thermoplastic coatings containing additives for enhancement of their biological and/or mechanical properties. A further object of this invention is to provide porous bioengineering thermoplastic coatings containing additives for increasing wear and abrasion resistance. Another object is to provide one or more processes for preparing coated prosthetic devices or anatomically shaped structures composed of bioengineering thermoplastics which have a porosity gradient. These and other objects will readily become apparent to those skilled in the art in the light of the teachings herein set forth.

In its broad aspect the present invention is directed to prosthetic devices coated with porous bioengineering thermoplastic materials having a porosity gradient which enables such devices to become firmly and permanently anchored into the musculoskelatal system by tissue ingrowth into the coated material. In one embodiment the prosthetic devices are comprised of a load bearing functional component and over at least a portion thereof, a porous coating of from about 0.5 to about 10 millimeters in thickness of a bioengineering thermoplastic material which is compatible with, and conducive to, the ingrowth of cancellous and cortical bone spicules, the coating having the following properties:

(a) a substantial portion of the coating having an average pore diameter of from about 90 to about 600 microns;

(b) pore interconnections having average, diameters of greater than about 50 micron;

(c) a modulus of elasticity from about 250,000 to about 500,000 pounds per square inch for non-reinforced, solid non-porous thermoplastic material, and from about 500,000 to about 3,000,000 pounds per square inch for reinforced, solid non-porous thermoplastic material;

(d) a total porosity of greater than about 20 percent and distributed such that a porosity gradient exists across the coating with the smallest pores on the side of the coating which contacts said load bearing functional component and the largest pores on the outer surface of the coating, and (e) a total creep strain of the non-reinforced, solid, non-porous thermoplastic material of less than one percent at a constant stress of 1,000 pounds per square inch at ambient temperature.

All of the properties being sufficient to enable stresses applied on the musculoskeletal system to be transferred to bone spicules within the pores of the material and maintain sufficient load and pore stability to promote irreversible ossification.

Prosthetic devices prepared by the process of this invention exhibit well defined directional porosity gradient affording improved biomechanical performance over those in U.S. Pat. No. 4,164,794. Specifically, a preferred higher level of porosity and greater average pore size is present at the outer surface of the coating where bone ingrowth must occur; increased material density (lower porosity), hence greater stiffness and strength, is located near the inside surface of the coating where stress levels are highest; and a smoother inside surface is obtained which results in more contact area with the metal implant thereby improving the coating/metal bond strength. Optimally reduced processing times can be attained because processing to achieve well defined porosity gradients relies on relatively high directional heating rates, conditions which must be avoided in methods used for making uniform porous parts.

As indicated in U.S. Pat. No. 4,164,794 the materials employed in the preparation of the prosthetic devices are classified as "bioengineering thermoplastics". One important feature of these materials is that their performance can be predicted by the use of metal design engineering equations for both long and short-term. These engineering design equations only apply up to the linear viscoelastic limit of the material. High density poyethylene has a linear viscoelastic limit of less than 0.1 percent and with this limit on the amount of strain, the allowable stress is minimal. In contrast, the linear viscoelastic limit of bioengineering thermoplastics, within the definition of this disclosure, is at least 1 percent strain. For example, one of the preferred engineering thermoplastic materials found to be suitable for the coatings of this invention is a polysulfone which has a 2 percent strain limit. Hence, the metal engineering design equations for both long and short term can apply up to this limit.

The unique characteristics of the bioengineering thermoplastic materials are more clearly evident when their performance is compared to polymeric materials previously disclosed as being useful for porous fixation devices. If the creep modulus varies extensively with time, deflection increased markedly, causing pore distortion and micro-displacement of a prosthesis under load. Creep tests have already been reported in the literature on porous high density polyethylene and a polytetrafluoroethylene-graphite composite, both of which have been indicated in the previously cited patents. It has been observed that significant changes in pore structure occurred upon compressive stresses as low as 80 psi for the porous polytetrafluoroethylene-graphite composites and at 300 psi for the porous high density polyethylene. Typical time to failure versus stress for the two reported high density polyethylene fabrications were under five minutes when stress levels greater than 300 psi were applied. It should be noted that this represents the stress levels that will be experienced in some orthopedic joint and device applications. The importance of maintaining pore geometries under loading environments was indicated earlier where it was observed that fibrous tissue is created in small pores. This is particularly critical in early postoperative periods prior to the ingrowth of bone when the porous polymeric coating on joint prostheses must have sufficient strength and rigidity to independently support applied load without assistance from ingrown bone. The strength of prior polymeric materials comes from the ingrown bone. Bioengineering thermoplastic porous coatings have strength like bone.

Each of these materials when prepared in accordance with the teachings of this invention provides coatings which have the physical properties hereinbefore enumerated. Illustrative of these materials are the polysulfones, such as, polyphenylsulfone, polyethersulfone, polyarylsulfones, and the like; polyphenylenesulfide, polyacetal, thermoplastic polyesters such as the aromatic polyesters, polycarbonates, aromatic polyamides, aromatic polyamideimides, thermoplastic polyimides and the polyaryletherketones, polyarylethernitriles, aromatic polyhydroxyethers, and the like. The most preferred materials for use in the invention are the aromatic polysulfones. These polysulfones contain repeating units having the formula:

wherein Ar is a divalent aromatic radical containing at least one unit having the structure:

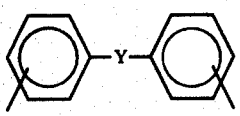

in which Y is oxygen, sulfur or the radical residuum of an aromatic diol, such as 4,4'-bis(p-hydroxyphenyl)-alkane. Particularly preferred polyarylene polyether polysulfone thermoplastic resins are those composed of repeating units having the structure shown below:

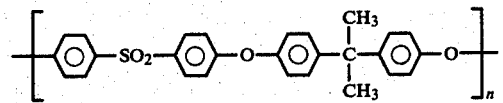

wherein n equals 10 to about 500. These are commercially available from Union Carbide Corporation as UDEL Polysulfones P-1700 and P-3703. These materials differ in that P-3703 has a lower molecular weight. Also useful are Astrel 360 a polysulfone sold by 3M Corporation and Polysulfone 200 P sold by ICI and Radel polyphenylsulfone sold by Union Carbide Corporation. Certain crystalline bioengineering thermoplastics like Stilan from Raychem Corporation, Polyarylene and Phenoxy A from Union Carbide Corporation, are also useful.

The materials which are employed in the present invention can also contain reinforcement materials, if so desired. Incorporation of glass, carbon or organic based fibers into the bioengineering thermoplastics extends the load-bearing and structural characteristics. Bioengineering thermoplastics exhibit bulk tensile or flexural modulus values in the range of 250,000–500,000 psi. Fiber reinforced products exhibit modulus values up to 3.0 million depending on the fiber type and loading. These values of modulus provide the intermediate range required for initial post-operative support and long-term stability of implanted prostheses in high load areas anchored by bone ingrowth.

Bioengineering thermoplastic coatings prepared by the process of this invention and having a porosity gradient across the coating thickness are apparent from the accompanying drawings wherein.

Figure 1:
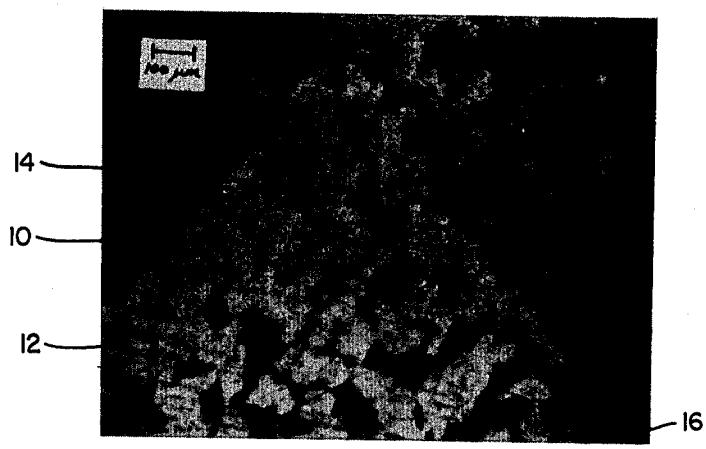
FIG. 1 is a photomicrograph of the cross-section of a porous polysulfone coating showing the inner surface.

With reference to FIG. 1, there is depicted at a magnification of 75 times the inner surface of a porous bioengineering thermoplastic coating prepared in accordance with the teachings of this invention. At the surface interface 10 between the porous coating 12 and solid support 14, the density of the sintered part is at its greatest. These sintered surface particles from essentially a skin or continuous coating which provides a maximum of surface area in contact with the support. Thus, improved adhesion to the support is obtained with resulting stiffness and strength where it is needed. Particles 16 which are distant from the surface interface 10 have a sintered configuration characterized by larger pores and interconnections, hence the greatest coating porosity.

Figure 2:
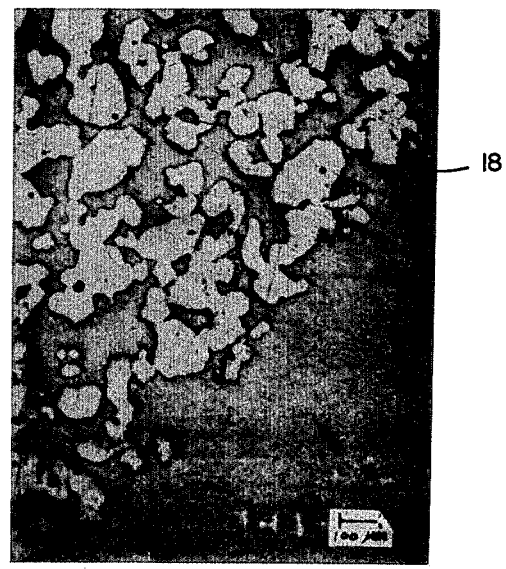
FIG. 2 is a photomicrograph of the cross-section of a porous coating showing the outer surface.

FIG. 2 is also a photomicrograph depicting the cross-section of a porous polysulfone coating at a magnification of 75 times and showing that the outer porosity of the coating is greatest at the outer surface 18 thus, provided ready access for bone ingrowth.

In practice, the prosthetic devices of this invention are conveniently prepared by a sintering technique whereby particles of the bioengineering thermoplastic material are heated in a particular sequence for a period of time and at a temperature sufficient to cause sintering that is, the particles fuse together at one or more contact points to provide a porous continuous composite material of the bioengineering thermoplastic having the desired porosity gradient and mechanical properties.

With regard to the desired mechanical properties it has been observed that the modulus of a porous material can be predicted through the Kerner equation or through a modified Halpin-Tsai equation. Hence, in order to achieve a material with a porosity, for example, of 55 percent, and an elastic modulus greater than 40,000 psi, the modulus of the starting polymer must exceed 200,000 psi. Thus, most polypropylenes, and all high density polyethylenes are incapable of being fabricated in a material of 55 percent porosity with a modulus of 40,000 psi. On the other hand since the modulus of solid polysulfone exceeds 340,000 psi, a material of 55 percent porosity whose modulus exceeds 70,000 psi can be obtained.

For the prosthetic devices of this invention it is preferred that the coatings have a porosity of greater than about 20 percent and still more preferably of from about 30 to about 70 percent.

Even though it was possible to predict the modulus of a thermoplastic having a desired porosity there was no simple method available to fabricate a material approaching these predictions which would be useful for the devices of this invention. It was unexpectedly found, however, that the desired degree of porosity could be obtained without sacrificing mechanical properties by the proper choice of particle size, molecular weight distribution and sintering conditions. All three are inter-related and necessary to achieve a coating or article having the necessary characteristics. For example, the sintering time and temperature which results in a desired pore size distribution may not produce the desired modulus of elasticity and/or tensile strength. Starting particle size distribution, sintering time, and temperature must be adjusted to achieve the desired balance of pore size, porosity, and mechanical properties.

With respect to particle size distribution, it has been found that sintered materials which meet the porosity and mechanical property requirements necessary for a successful prosthetic device can be made through the use of either a single particle size or a bimodal distribution of particle sizes.

In practice, a mixture of particle sizes wherein the ratio of particle diameters ranges from about 7:1 to about 5:1 has been found to be acceptable for porous coatings greater than 2 millimeters in thickness. Particle sizes of from about 300 microns to about 50 microns are particularly preferred. For example, a mixture of particles which are retained on a 50 mesh screen (U.S. Standard Sieve) and pass through a 270 mesh screen have provided coatings and articles having the desired porosity and biomechanical features. It has also been observed that optimum results are achieved when the ratio of fine to coarse particle size ranges from about 40 to about 60 weight percent.

For porous sintered coatings which are on the order of 0.5 to about 2.0 millimeters thick, particles which pass through a 40 mesh screen and are retained on a 70 mesh screen (average particle size of 320μ) have been found to provide the most advantageous mechanical and biological characteristics.

As previously indicated, the sintering conditions are particularly important not only to achieve the desired overall porosity of the coating, but to achieve in the same operation, the desired porosity gradient. In general, sintering has been accomplished by charging a metal mold with powder and heating the mold to a prescribed sintering temperature, $T_s$, greater than the glass transition temperature, $T_g$, and less than the melting or melt processing temperature, $T_m$, (i.e. $T_g < T_s < T_m$). The sintering temperature is held constant for a given time, t. Essentially, no pressure, other than that induced by differential thermal expansion, is applied. The application of pressure at $T_s$ leads to fluxing of the material. This indicates that if pressure is applied, lower temperatures and shorter time cycles must be employed to retain porosity in the sintered parts.

However, in contrast to the sintering technique disclosed in U.S. Pat. No. 4,164,794 wherein heating was employed to achieve homogeneous sintering to maintain approximate uniformity of porosity throughout the coating, this invention utilizes high heating rates with controlled directional heat flow and hence provides a well defined porosity gradient. By utilizing high heating rates, a temperature gradient exists within the sintering powder resulting in lower porosity in the region of higher temperature. Thus an ordered porous structure is obtained by the use of directional heating, i.e., driving heat from the inside to the outside during the sintering-bonding process.

Depending upon the particular prosthetic device being coated, one or more techniques can be employed to effect the differential heating. For example a sleeve of the sintered porous material can be prepared separately from the prosthesis and affixed to the device by means of adhesives and/or shrinkage. As indicated in Example 2 a sleeve of sintered material is conveniently prepared in an insulated mold wherein the core is heated first to develop a 'skin' at its inside surface which conforms tightly to the shape of the core and has a low porosity adjacent to the interface. Heating can be effected by several methods such as passing a heated silicone oil through the interior of the core.

After the inside heating is completed, the insulation is removed and the mold is heated either on the inside and outside simultaneously or on the outside only. This is continued until the sintering is completed and the material has the desired pore structure and mechanical properties. Once the material is sufficiently cool, it is then removed from the core. The free-standing sintered sleeve can then be applied to a metal implant by dip-coating the implant with a film of PSF-Silyl Reactive (PSF-SR) which is subsequently cross-linked at 270° C. for 10-15 minutes. The implant then receives a film of PSF-1700 M.G., also by a dip-coating method and is dried. Once this film has dried the stem is again dipped in a PSF-1700 M.G. solution (5% to 10% PSF-1700 M.G. in $CH_2Cl_2$) and the porous sleeve is slid into place while the PSF 'adhesive' is still tacky. The completed prosthesis is then dried and cleaned. Following sterilization it is ready to be surgically implanted with an interference fit.

Other methods can also be employed particularly where the implants are non-uniform or too small to heat from the inside. For example, as indicated in Example 3, it has been observed that some human hip prostheses have dimensional variations between the same model. Rather than machine a new mold for each implant, induction heating can be used.

The major difference between this technique and the previous one is that the implant itself is used as the 'male' or core section of the mold, and the powder is heated from the outside first and then from the inside. Sintering from the inside is achieved by inductively heating the implant.

The implant stem is prepared for bonding by applying and curing a film of PSF-SR onto it and then applying and drying a film of PSF-1700 M.G. The implant is then inserted into the mold cavity and secured. Thereafter, the gap (1 mm wide or greater) between the implant stem and the mold cavity walls is filled with PSF-1700 M.G. powder of the desired particle size distribution. The outside of the mold is then raised to the sintering temperature by heating with, for example, a band heater, electrical resistance heater tape or an induction coil if the mold is made of appropriate material. The outside heat is maintained for a short time only. An undersintered, oversized preform results because the polymer powder sinters most at the surface of the cavity and shrinks away from the implant. Once the preform has enough integrity to maintain its shape, the cavity section of the mold is split and removed. This leaves the oversized coating on the implant. The implant and coating are then placed within an induction coil designed to provide uniform heating of the metal implant surface. The implant is inductively heated to the appropriate temperature for sintering and maintained until sintering is completed and the coating has shrunk to conform tightly to the surface of the implant and bond to it. The coated prosthesis is then cooled and cleaned. Following sterilization it is ready to be surgically implanted.

The porous sintered coatings of this invention having a porosity gradient are also useful for the root cores of dental implants. However, due to the small size of the implants it was not practical to heat from the inside only. Accordingly, a mold was designed so that a temperature gradient of sufficient magnitude was achieved. The mold consisted of a top plate, a mold body and a bottom plate. The bottom plate has one or more cavities to receive the implant to be coated in an upside down position. Thus the implant is placed with the part of the abutment to be coated facing up. The mold body is then placed on top of the bottom plate and has openings which line up with the upright posts. Thereafter the gap between the cores or posts and the cavity walls of the mold body are filled with polymer powder of the desired particle size distribution. The powder is introduced through holes in the top of the mold body and are tamped to make sure the entire gap is well filled. The top plate is then put in place and secured with cap screws. The mold which is encircled with insulation is placed in a press of which the platens have been preheated. The top platen is heated to 40° C. below the desired sintering temperature and the bottom platen is heated at 40° C. above the desired sintering temperature. These settings cause the titanium root cores to heat up first and subsequently maintain a higher temperature than the cavity walls of the mold body. This results in extremely good conformity of the inside surface of the porous coating with the outside surface of the core to which it must bond. After the mold has reached the desired temperature and been maintained there for the required period of time, the mold is removed from the press and cooled. The completed implants are removed from the mold and cleaned. Following sterilization the artificial tooth roots are ready to be surgically implanted.

The load bearing functional component of the prosthetic devices of this invention can be comprised of a variety of metals and alloys known in the art. While titanium and tantalum are, for the most part, the only pure metals considered as safe for internal use, a variety of alloys have found general acceptance. Stainless steels, cobalt-base alloys and titanium based alloys all are tolerated by the body as well as being corrosion resistant and fabricated into desired shape.

For some applications it may be desirable to incorporate additives which increase the wear and abrasion resistance of the prosthesis. Carbon fiber, graphite fiber, Teflon, molybdenum disulfide are useful additives which afford wear resistant engineering thermoplastics equal or superior to self-lubricated materials typically used in commercially available joint prostheses. Compositions with carbon fiber are preferred for the injection molding or machining of articulating prosthesis such as acetabular cups, tibial, and glenoid components of total knee and shoulder replacements.

The sintered coatings of this invention can be bonded to the load-bearing functional component by several methods. For example, silyl reactive polymers like silyl reactive polysulfone are utilized for bonding porous polymeric coatings to metal substrates. Silyl reactive polysulfone (PSF-SR) resins possess three important features. First, the presence of hydrolyzable silane end groups provides an inherent coupling ability to metallic surfaces. Second, the PSF-SR resins have a low melt (or solution) viscosity which greatly facilitates "wetting" during the formation of adhesive bonds. Third, they are polymeric adhesives which exhibit no solubility in physiological fluids and hence have no biological/toxicological effects when implanted. Other techniques such as heat shrinking a partially sintered sleeve can also be employed.

EXAMPLE 1

Effect of Sintering Conditions on Pore Size

This experiment illustrates the effect of sintering conditions (i.e. particle size, time and bath temperature) without any attempt to achieve a porosity gradient. For this experiment simple molds were fabricated from ⅜ inch outer diameter steel tubing. The tubing was cut to a 6 inch length and fitted with threaded end plugs. Wall thickness of the tubing was approximately 0.038 inch. The resulting sintered plastic part had a diameter of 0.300 inch and was 6 inches long. This proved to be a convenient sample size for tensile property characterization.

PSF-3703 powder with the particle size distribution shown in Table I below was used. This material was sintered according to the following schedule: pack powder in a mold; immerse mold in an oil bath at 220° C. for various times ranging from 10 to 30 min. The resulting rod of 0.300 inch diameter was then cut to sample lengths of 2.5 inches.

Interconnecting pore size distribution was then determined through mercury intrusion porosimetry. Data are reported in Table I. Characteristic pore size is shown as the percentage of pores larger than or equal to 132$\mu$. As the time at temperature is increased from 10 to 30 minutes, the number of pores $\geq$132 $\mu$ in diameter increases. However, if the material is held at 220° C. for times greater than 30 minutes, the resulting sample would no longer be porous. On the other hand, if the material were exposed to temperature for less than 10 minutes, little or no sintering would have occurred. Thus, there is an optimum time at temperature and temperature for a given particle size and molecular weight distribution to achieve a desired pore size.

TABLE I

| U.S. SCREEN | DISTRIBUTION |
|---|---|
| % on 35 | — |
| on 40 | Trace |
| on 50 | — |
| on 60 | 14.0 |
| on 80 | 50.0 |
| on 100 | 18.0 |
| thru 100 | — |
| on 140 | 10.0 |
| on 230 | 4.0 |
| thru 230 | 4.0 |

| Sintering Time at 220° C. (Min.) | % Pore Volume $\geq$132$\mu$ |
|---|---|
| 10 | 49.4 |
| 12 | 52.6 |
| 14 | 56.5 |
| 16 | 58.1 |
| 18 | 61.8 |
| 20 | 69.5 |
| 30 | 75.4 |

EXAMPLE 2

Effect of Heating Sequence on Porosity

In this experiment a male-female mold was fabricated from steel tubing of different internal diameters. The male member had an external diameter of 0.25 inch and fitted inside a larger diameter female member having an internal diameter of 0.50 inch. The mold was arranged so that heated oil could flow through the interior, hollow portion of the male member and the entire mold heated by separate means from the outside.

The gap between the core and cavity sections of the mold was then filled with the polymer powder of the desired particle size distribution. The powder was not compacted as in standard powder-metallurgy sintering techniques. With the outside of the mold insulated, silicone oil at a temperature of 250° C. was run through the male member of the mold for a period of 15 minutes. Thereafter the insulation was removed and the outside was heated using an electrical heating tape until the outside temperature reached 240° C. These temperatures were maintained for approximately 10 minutes. Upon cooling a sintered sleeve was removed from the mold and found to have a porosity gradient similar to that shown in FIGS. 1 and 2.

EXAMPLE 3

Sintering of Conformal Porous Coating by Heating Implant Itself

Due to the dimensional variations (as much as 0.050" to 0.060") which were found to exist between different human hip implants of the same model, it would be necessary to machine a new mold for each hip to be coated. This example demonstrates a process which involves induction heating of the implant itself, providing for the simultaneous sintering and bonding of the coating. It was thus possible to coat prostheses which, because of their geometry, would not allow a conformal presintered sleeve to be applied in one piece. The major difference between this technique and the previous one is that the implant itself is used as the 'male' or core section of the mold, and the powder is heated from the outside first and then from the inside. Sintering from the inside is achieved by inductively heating the implant.

The implant stem is prepared for bonding by applying and curing a film of PSF-SR onto it and then applying and drying a film of PSF-1700 M.G. The implant is then inserted into the mold cavity and secured. The gap (1 mm wide or greater) between the implant stem (core) and the mold cavity walls is filled with PSF-1700 M.G. powder of the desired particle size distribution. The outside of the mold is then raised to the sintering temperature and maintained for a short time only. An undersintered, oversized preform results because the polymer powder sinters most at the surface of the cavity and shrinks away from the implant. Once the preform has enough integrity to maintain its shape, the cavity section of the mold is split and removed. This leaves the oversized coating on the implant. The implant and coating are then placed within an induction coil designed to provide uniform heating of the metal implant surface. The implant is inductively heated to the appropriate temperature for sintering and maintained until sintering is completed and the coating has shrunk to conform tightly to the surface of the implant and bond to it. The coated prosthesis is then cooled and cleaned. Following sterilization it may be surgically implanted. The sinter/shrink/bond step has also been evaluated by heating an implant in a hot air oven to 255° C. with the stem pointing up. The preform porous sleeve was then slipped onto the hot stem, allowed to complete its sintering and shrink until it fit tightly. Even without the adhesive bond the porous coatings have been difficult to remove.

Although the invention has been illustrated by the preceding examples, it is not to be construed as being limited to the materials employed therein, but rather the invention relates to the generic area as hereinbefore disclosed. Various modifications and embodiments can be made without departing from the spirit and scope thereof.

What is claimed is:

1. A prosthetic device comprised of a load bearing functional component and, over at least a portion thereof, a porous coating of a bioengineering thermoplastic material which is compatible with, and conducive for, the ingrowth of bone spicules, said material being selected from the group consisting of polysulfones, polyphenylenesulfides, polyacetals, thermoplastic polyesters, polycarbonates, aromatic polyamides, aromatic polyamideimides, thermoplastic polyimides, polyaryletherketones, polyarylethernitriles and aromatic polyhydroxyethers, and having the following properties:
    (a) a substantial portion of the coating having an average pore diameter of from about 90 to about 600 microns;
    (b) pore interconnections having average diameters of greater than about 50 microns,
    (c) a modulus of elasticity from about 250,000 to about 500,000 pounds per square inch for non-reinforced, solid non-porous thermoplastic material, and from about 500,000 to about 3,000,000 pounds per square inch for reinforced, solid non-porous thermoplastic material;
    (d) a total porosity of greater than about 20 percent and distributed such that a porosity gradient exists across the coating with the smallest pores on the side of the coating which contacts said load bearing functional component and the largest pores on the outer surface of the coating, and
    (e) a total creep strain of the non-reinforced, solid, non-porous thermoplastic material of less than one percent at a constant stress of 1,000 pounds per square inch at ambient temperature, all of the properties being sufficient to enable stresses applied on the musculoskeletal system to be transferred to bone spicules within the pores of the material and maintain sufficient load and pore stability to promote irreversible ossification.

2. The device of claim 1 wherein said porous coating is from about 0.5 to about 10 millimeters in thickness.

3. The device of claim 1 wherein said thermoplastic material is reinforced and has a modulus of elasticity of from about 500,000 to about 3,000,000 pounds per square inch.

4. The device of claim 1 wherein said thermoplastic material is not reinforced and has a modulus of elasticity from about 250,000 to about 500,000 pounds per square inch.

5. The device of claim 1 wherein said thermoplastic material has a porosity of from about 30 to about 70 percent.

6. The device of claim 1 which is a total hip prosthesis.

7. The device of claim 1 which is an endosteal blade implant or other dental implant.

8. The device of claim 1 which is an intramedullary nail.

9. The device of claim 1 which is a cancellous screw.

10. The device of claim 1 which is a cortical screw.

11. The device of claim 1 within said load bearing functional component is comprised of a stainless steel.

12. The device of claim 1 wherein said load bearing functional component is comprised of a cobalt based alloy.

13. The device of claim 1 wherein said load of bearing functional component is comprised of a titanium based alloy.

14. The device of claim 1 wherein said engineering thermoplastic material is a polysulfone.

15. The device of claim 1 wherein said engineering thermoplastic material is a polyarylsulfone.

16. The device of claim 1 wherein said engineering thermoplastic material is a polyphenylsulfone.

17. The device of claim 1 wherein said engineering thermoplastic material is a polyethersulfone.

18. The device of claim 1 wherein said engineering thermoplastic material is a polycarbonate.

19. The device of claim 1 wherein said engineering thermoplastic material is an aromatic polyamide.

20. The device of claim 1 wherein said engineering thermoplastic material is an aromatic polyhydroxyether.

* * * * *